(12) United States Patent
Viswanathan et al.

(10) Patent No.: US 10,799,206 B2
(45) Date of Patent: Oct. 13, 2020

(54) SYSTEM AND METHOD FOR CALIBRATING AN IMAGING SYSTEM

(71) Applicant: GENERAL ELECTRIC COMPANY, Schenectady, NY (US)

(72) Inventors: Srikrishnan Viswanathan, Bangalor (IN); Arun Kumar Chandrashekarappa, Bangalor (IN); Nasir Ahmed Desai, Bangalor (IN); Xin Li, Beijing (CN); Bin Ye, Beijing (CN); Qingyong Ding, Beijing (CN); Youyou Chen, Beijing (CN)

(73) Assignee: General Electric Company, Schenectady, NY (US)

( * ) Notice: Subject to any disclaimer, the term of this patent is extended or adjusted under 35 U.S.C. 154(b) by 82 days.

(21) Appl. No.: 16/146,308

(22) Filed: Sep. 28, 2018

(65) Prior Publication Data
US 2020/0100758 A1 Apr. 2, 2020

(51) Int. Cl.
*A61B 6/00* (2006.01)
*A61B 6/02* (2006.01)
*A61B 6/08* (2006.01)

(52) U.S. Cl.
CPC .......... *A61B 6/587* (2013.01); *A61B 6/08* (2013.01); *A61B 6/4452* (2013.01); *A61B 6/4464* (2013.01); *A61B 6/547* (2013.01); *A61B 6/585* (2013.01)

(58) Field of Classification Search
CPC ....... A61B 6/08; A61B 6/4452; A61B 6/4464; A61B 6/547; A61B 6/585; A61B 6/587
See application file for complete search history.

(56) References Cited

U.S. PATENT DOCUMENTS

| | | |
|---|---|---|
| 9,524,582 B2 | 12/2016 | Ma et al. |
| 9,589,336 B2 | 3/2017 | Flohr et al. |
| 9,633,435 B2 | 4/2017 | Ma et al. |
| 9,659,409 B2 | 5/2017 | Siebarth et al. |
| 9,665,936 B2 | 5/2017 | Kluckner et al. |

(Continued)

FOREIGN PATENT DOCUMENTS

WO    2018075053 A1    4/2018

OTHER PUBLICATIONS

Carmody, Tim, "How Motion Detection Works in Xbox Kinect", Wired magazine, Nov. 3, 2010, [online], https://www.wired.com/2010/11/tonights-release-xbox-kinect-how-does-it-work/, retrieved on May 19, 2020. (Year: 2010).*

*Primary Examiner* — Mark R Gaworecki

(57) ABSTRACT

A method of calibrating a system for imaging a subject is provided. The method includes determining a position of an X-ray source of the system operative to transmit X-rays through the subject; and calibrating the position of the X-ray source with respect to a detector of the system, based at least in part on a field of view of the X-ray source, the detector operative to receive the X-rays transmitted by the X-ray source. In embodiments, the method includes positioning an X-ray source of the system via a controller at one or more calibration positions based at least in part on at least one camera of the system. In such embodiments the X-ray source is disposed on a mobile arm and operative to transmit X-rays through the subject, and a field of view of the X-ray source is directed substantially towards the detector at each of the calibration positions.

11 Claims, 12 Drawing Sheets

(56) References Cited

U.S. PATENT DOCUMENTS

| | | |
|---|---|---|
| 9,710,141 B2 | 7/2017 | Braun et al. |
| 9,895,131 B2 | 2/2018 | Chang et al. |
| 9,898,858 B2 | 2/2018 | Tamersoy et al. |
| 9,962,138 B2 | 5/2018 | Schweizer |
| 2004/0105526 A1* | 6/2004 | Zhang .................. A61B 6/4452 378/205 |
| 2005/0265516 A1 | 12/2005 | Haider |
| 2008/0130835 A1 | 6/2008 | Peterson et al. |
| 2011/0224904 A1 | 9/2011 | Feiten et al. |
| 2016/0128666 A1 | 5/2016 | Grasruck et al. |
| 2016/0202864 A1 | 7/2016 | Hardie et al. |
| 2016/0203265 A1 | 7/2016 | Hardie et al. |
| 2016/0235386 A1 | 8/2016 | Schweizer |
| 2016/0262713 A1 | 9/2016 | Flohr et al. |
| 2016/0296185 A1 | 10/2016 | Gemmel et al. |
| 2016/0367169 A1 | 12/2016 | Hardie et al. |
| 2017/0000446 A1 | 1/2017 | Brinker et al. |
| 2017/0100089 A1* | 4/2017 | Chang ..................... A61B 6/54 |
| 2017/0165501 A1 | 6/2017 | Rapaka et al. |
| 2017/0200317 A1 | 7/2017 | Hannemann et al. |
| 2017/0224298 A1 | 8/2017 | Hannemann et al. |
| 2017/0354385 A1 | 12/2017 | Lerch |
| 2018/0063386 A1 | 3/2018 | Sharma et al. |

* cited by examiner

SYSTEM AND METHOD FOR CALIBRATING AN IMAGING SYSTEM

BACKGROUND

Technical Field

Embodiments of the invention relate generally to medical imaging systems, and more specifically, to systems and methods for calibrating an imaging system.

Discussion of Art

Many imaging devices/systems acquire medical diagnostic images of a subject/patient or other object/region of interest by transmitting X-rays, through the subject or object via an X-ray source and receiving the X-rays at an X-ray detector disposed on the opposite side of the subject from the X-ray source. Many such medical imaging systems have X-ray sources that are mounted to an overhead tube suspension system ("OTS") which provides for three-dimensional ("3D") movement of the X-ray source about the subject. In many such imaging systems, referred to herein as "OTS imaging systems", the X-ray source is mounted to a mobile arm mounted to a carriage that traverses the ceiling via rails fixed to the ceiling of the room containing the OTS imaging system.

Many OTS imaging systems have positioning systems that track the location and/or orientation of the X-ray source with respect to one or more detectors, e.g., a wall stand detector or table detector. Due to variations in the orientation of the rails along the ceiling, which may occur during installation and/or over time by warping/shifting of the ceiling, the positioning system of some OTS imaging systems may become misaligned, i.e., unable to accurately reflect the true position and/or orientation of the X-ray source. As will be understood, misaligned positioning systems typically result in deficient images of a subject.

Additionally, many OTS imaging systems take several images of the subject at several different locations. Such OTS imaging systems, however, often require a technician to manually calibrate the positioning system at each location to ensure that the distance from the detector and/or subject to the X-ray source is accurate. Manual calibration of an OTS imaging system at several locations, however, is a tedious time consuming task which is also subject to human error.

What is needed, therefore, is an improved system and method for calibrating an imaging system.

BRIEF DESCRIPTION

In an embodiment, an X-ray system is provided. The X-ray system includes an X-ray source, a detector, and a controller. The X-ray source is operative to transmit X-rays through a subject. The detector is operative to receive the X-rays. The controller is operative to determine a position of the X-ray source, and to calibrate the position of the X-ray source with respect to the detector based at least in part on a field of view of the X-ray source.

In another embodiment, a method of calibrating an X-ray imaging system is provided. The method includes determining a position of an X-ray source of the system operative to transmit X-rays through a subject. The method further includes calibrating the position of the X-ray source with respect to a detector of the system based at least in part on a field of view of the X-ray source. The detector is operative to receive the X-rays transmitted by the X-ray source.

In yet another embodiment, a non-transitory computer-readable medium storing instructions is provided. The stored instructions adapt a controller to generate one or more edge points of a field of view of an X-ray source of a system for imaging a subject with respect to a detector of the system, and to generate one or more edge distances of the field of view with respect to a center of the detector. The stored instructions further adapt the controller to generate one or more offset values via comparing the one or more edge points to the one or more edge distances, and to adjust the field of view based at least in part on the one or more offset values.

In yet another embodiment, a controller for calibrating a system for imaging a subject is provided. The controller is operative to generate one or more edge points of a field of view of an X-ray source of the system with respect to a detector of the system, and to generate one or more edge distances of the field of view with respect to a center of the detector. The controller is further operative to generate one or more offset values via comparing the one or more edge points to the one or more edge distances, and to adjust one or more parameters of the system based at least in part on the one or more offset values, the one or more parameters determining, in part, the field of view.

In yet another embodiment, a system for imaging a subject is provided. The system includes an X-ray source, a detector, at least one camera, and a controller. The X-ray source is disposed on a mobile arm and operative to transmit X-rays through the subject. The detector is operative to receive the X-rays transmitted by the X-ray source. The controller is operative to position the X-ray source via the mobile arm at one or more calibration positions based at least in part on the at least one camera such that a field of view of the X-ray source is directed substantially towards the detector at each of the calibration positions.

In yet another embodiment, a method of calibrating a system for imaging a subject is provided. The method includes positioning an X-ray source of the system via a controller at one or more calibration positions based at least in part on at least one camera of the system. The X-ray source is disposed on a mobile arm and operative to transmit X-rays through the subject. A field of view of the X-ray source is directed substantially towards the detector at each of the calibration positions.

In yet another embodiment, a non-transitory computer readable medium storing instructions is provided. The stored instructions adapt a controller to position an X-ray source of a system for imaging a subject at one or more calibration positions based at least in part on at least one camera of the system. The X-ray source is disposed on a mobile arm and operative to transmit X-rays through the subject. A field of view of the X-ray source is directed substantially towards the detector at each of the calibration positions.

DRAWINGS

The present invention will be better understood from reading the following description of non-limiting embodiments, with reference to the attached drawings, wherein below:

Figure 1:
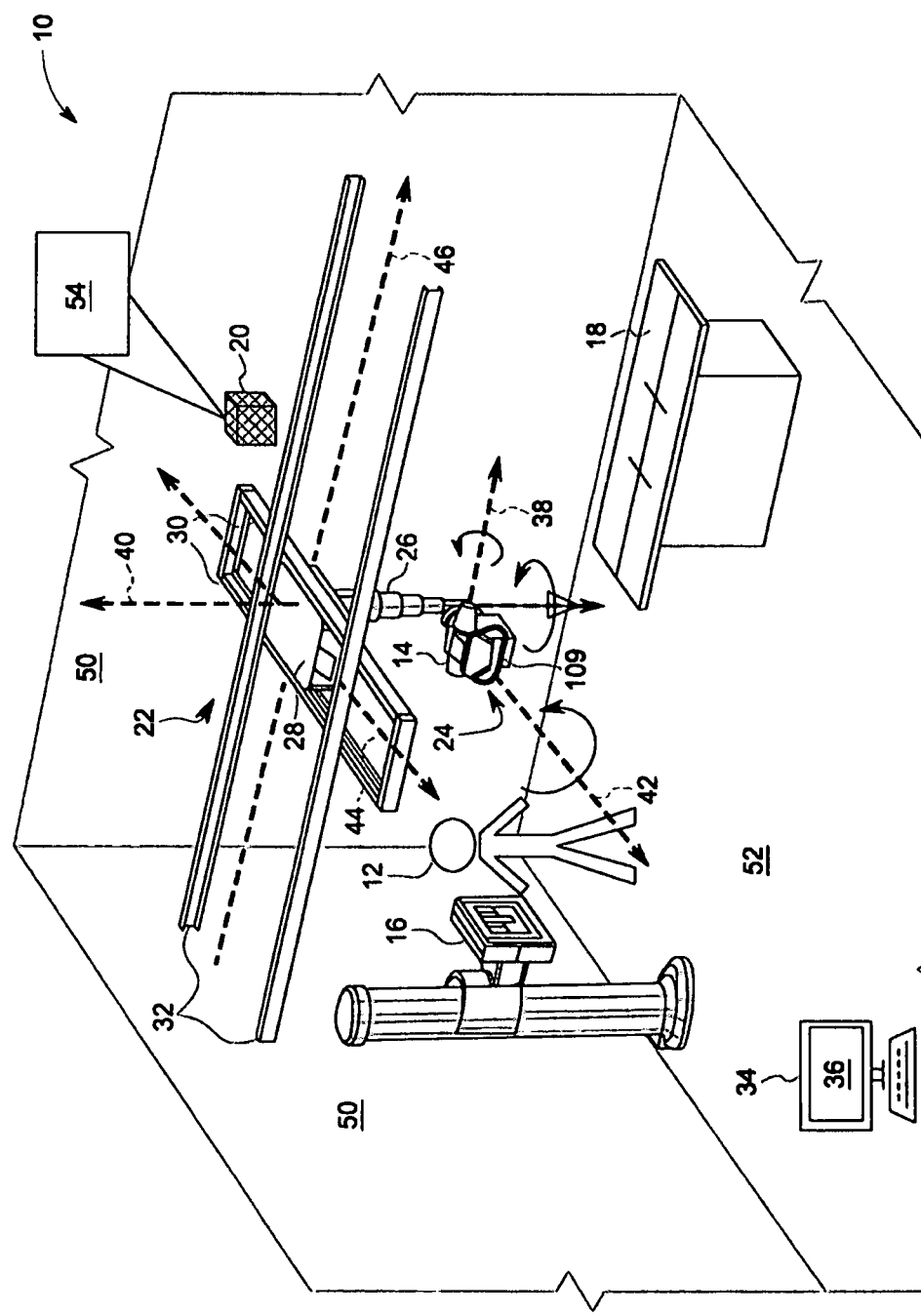
FIG. 1 is a diagram of an imaging system that includes a system for calibrating the imaging system, in accordance with an embodiment of the present invention.
Figure 18:
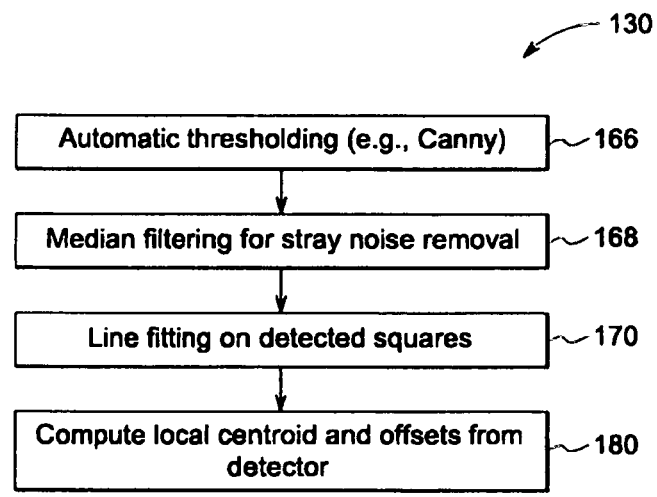
Figure 19:
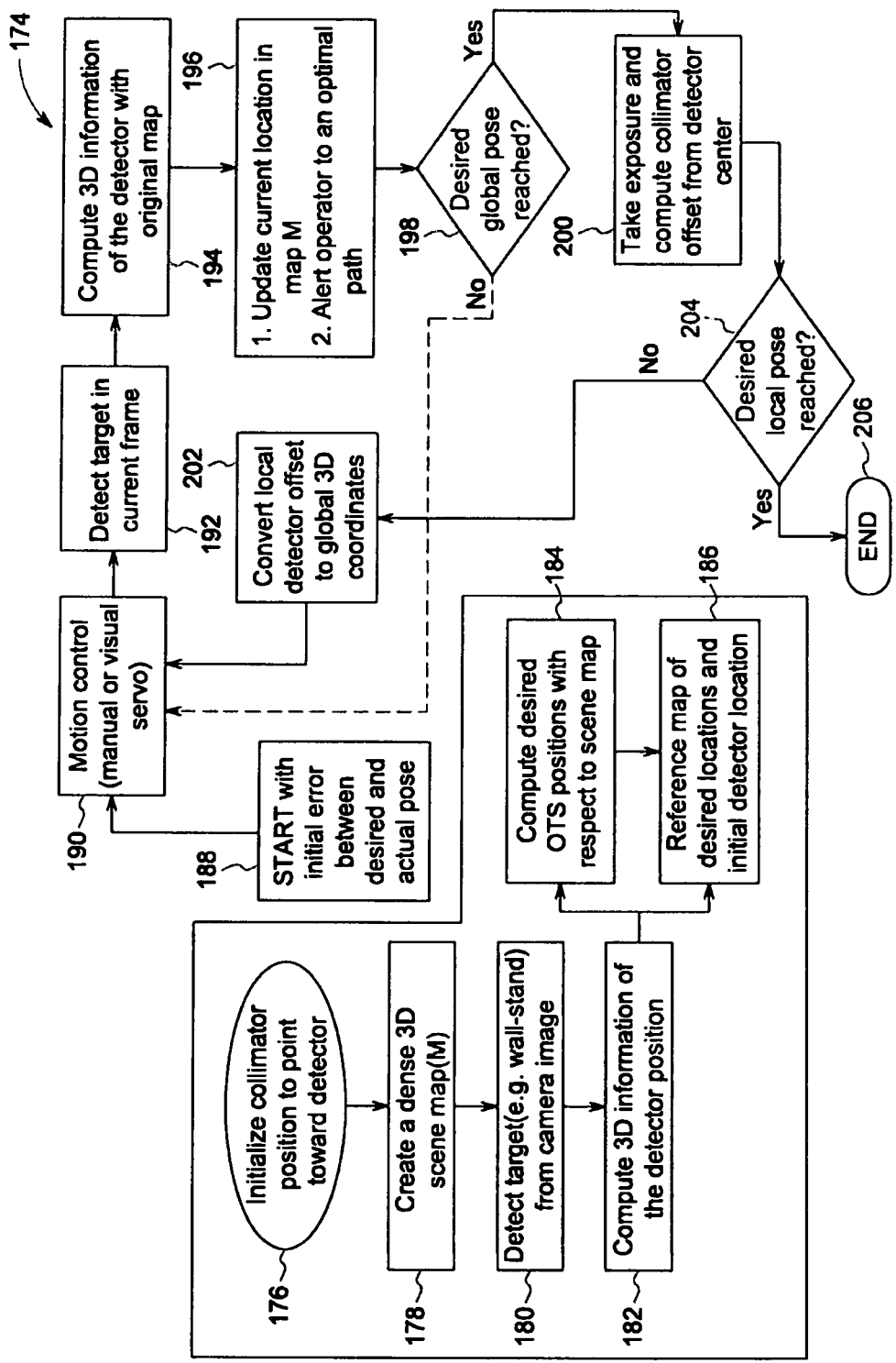

FIG. 18 is a flow chart depicting yet another method of calibrating the imaging system of FIG. 1 utilizing the system for calibrating the imaging system, in accordance with an embodiment of the present invention; and FIG. 19 is a flow chart depicting still yet another method of calibrating the imaging system of FIG. 1 utilizing the system for calibrating the imaging system, in accordance with an embodiment of the present invention.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. The term "translational variance", as used herein, refers to a difference between an indicated position of an X-ray source of an OTS imaging system, as indicated by a positioning system of the OTS imaging system, and an actual position of the X-ray source. As will be understood, translational variances may occur in two-dimensional ("2D") and/or 3D space. Similarly, the term "angular variance", as used herein, refers to an angular difference between an indicated central direction/vector of a FOV of an X-ray source of an OTS imaging system, as indicated by a positioning system of the OTS imaging system, and an actual central direction/vector of the FOV. Angular variances may occur in 2D and/or 3D space. The term "misaligned", as used herein with respect to an OTS imaging system and/or a positioning system of the OTS imaging system, refers to a scenario where the OTS imaging system is experiencing an angular and/or translational variances, i.e., the positioning system does not indicate/know the true position of the X-ray source and/or the true orientation of the X-ray source's FOV. The terms "aligned" and "calibrated", as used herein with respect to an OTS imaging system and/or a positioning system of the OTS imaging system, refer to a scenario where the OTS imaging system is not experiencing an angular and/or translational variance, i.e., the positioning system indicates/knows the true position of the X-ray source and/or the true orientation of the X-ray source's FOV. The term "operational mode", as used herein with respect to an OTS imaging system, refers to a configuration of the OTS imaging system that provides for scanning of a subject/patient. The term "service mode", as used herein with respect to an OTS imaging system, refers to a configuration of the OTS imaging system which does not provide for scanning of a subject/patient but does provide for changes to the configuration of the OTS imaging system, e.g., a configuration which provides for annual or bi-annual maintenance of the OTS imaging system.

As will be explained in greater detail below, embodiments of the present invention provide for systems and methods of calibrating an OTS imaging system, e.g., calibration of an positioning system for the OTS imaging system, to correct for translational and/or angular variances caused during installation of the OTS imaging system, translational and/or angular variances resulting from ceiling warping and/or shifting over time, and/or other types of translational and/or angular variances which may cause the positioning system of an OTS imaging system to become misaligned, e.g., mechanical deformation of one or more components of the OTS imaging system.

Further, as will also be explained in greater detail below, some embodiments of the present invention provide for systems and methods of calibrating a positioning system for an OTS imaging system at each location of a multi-location imaging sequence.

Additionally, while the embodiments disclosed herein are described with respect to an X-ray based imaging system, it is to be understood that embodiments of the present invention are equally applicable to imaging systems that emit other types of electromagnetic radiation, e.g., radio waves, infrared light, optical light, etc.; sound waves; and/or other particles/objects capable of producing images, and/or other devices and/or imaging systems which require a device, e.g., an X-ray source, to be aligned with a subject and/or detector. Further, embodiments of the present invention related imaging systems may be used to analyze objects within any material which can be internally imaged, generally. As such, embodiments of the present invention are not limited to analyzing objects within human tissue.

Accordingly, referring now to FIG. 1, the major components of an imaging system 10 for imaging a subject 12, in accordance with an embodiment of the present invention, is shown. The system 10 includes an X-ray source 14, e.g., X-ray tube/generator, one or more detectors, e.g., wall stand detector 16 and/or table detector 18, and a controller 20. The X-ray source 14 may be disposed in an OTS 22. In embodiments, the OTS 22 includes a tube mounting assembly 24, which secures the X-ray source 14 to a mobile arm 26 fixed to a carriage 28. The carriage 28, in turn, may be mounted to one or more translational positioning systems, e.g., horizontal positioning rails 30 and/or longitudinal positioning rails 32. In embodiments, the system 10 may further include a workstation 34 that provides for a human machine interface ("HMI") 36, e.g., a graphical user interface ("GUI"), for facilitating operation of the system 10 by a technician.

The X-ray source 14 is operative to transmit X-rays through the subject 12, which is received by at least one of the detectors 16 and 18 so as to generate an image of the subject 12. In embodiments, the detectors 16 and/or 18 may be film based and/or digital based. When digital based, the detectors 16 and/or 18 may electronically communicate with the controller 20 to provide the controller 20 with a list/array of pixels that the controller 20 can generate an image from.

As will be understood, the OTS 22 provides for 3D movement of the X-ray source 14 about the subject 12 and detectors 16, 18. For example, in embodiments, the tube mounting assembly 24 may independently rotate along tilting axis 38, panning axis 40, also referred to herein as the "z-axis", and/or rotational axis 42. The mobile arm 26 may provide for vertical movement of the tube mounting assembly 24 along the z-axis 40. For example, the mobile arm 26 may be telescoping, e.g., nesting subsections, and/or move along the z-axis 40 via gears, cogs, chains, and/or other suitable mechanisms. The carriage 28 may provide for translational movement of the tube mounting assembly 24 along an "x-axis" 44 via the horizontal positioning rails 30, and/or for movement along a "y-axis" 46 via the longitudinal positioning rails 32.

The horizontal 30 and/or longitudinal 32 positioning rails may be mounted to a ceiling 48 (omitted in FIG. 1 for clarity and shown in FIGS. 2, 3, 6, 7, and 8). For example, as shown in FIG. 1, the longitudinal positioning rails 32 may be mounted to the ceiling 48 with the horizontal positioning rails 30 slidably mounted to the longitudinal positioning rails 32. As will be understood, however, in embodiments, the horizontal positioning rails 30 may be mounted to the ceiling 48 with the longitudinal positioning rails 32 slidably mounted to the horizontal positioning rails 30. Further, while the OTS 22 is depicted herein as being secured to the ceiling 48, it will be understood that, in other embodiments, the OTS 22 may be secured to a side wall 50 and/or to the floor 52. In other words, the horizontal 30 and/or longitudinal 32 positioning rails may be mounted to/supported by other structures besides the ceiling 48, e.g., a mobile gantry and/or supporting framework. Further still, while FIG. 1 depicts the x-axis 44, y-axis 46, and z-axis 40 as orthogonal, it will be understood that the axes 44, 46, 40 may intersect each other at other angles. Thus, the OTS 22 can position the X-ray source 14 at any position along the x-axis 44, y-axis 46 and z-axis 40 with any orientation in the space formed by the tilt axis 38, pan axis 40, and rotational 42.

Accordingly, in embodiments, the system 10 may further include a positioning system 54 facilitated by the controller 20. The positioning system 54 may track the location and/or orientation of the X-ray source 14. In embodiments, the positioning system 54 may electronically communicate with the workstation 34 to convey to a technician the location and/or orientation of the X-ray source 14, and/or to provide for control over the OTS 22 via the HMI 36.

Figure 2:
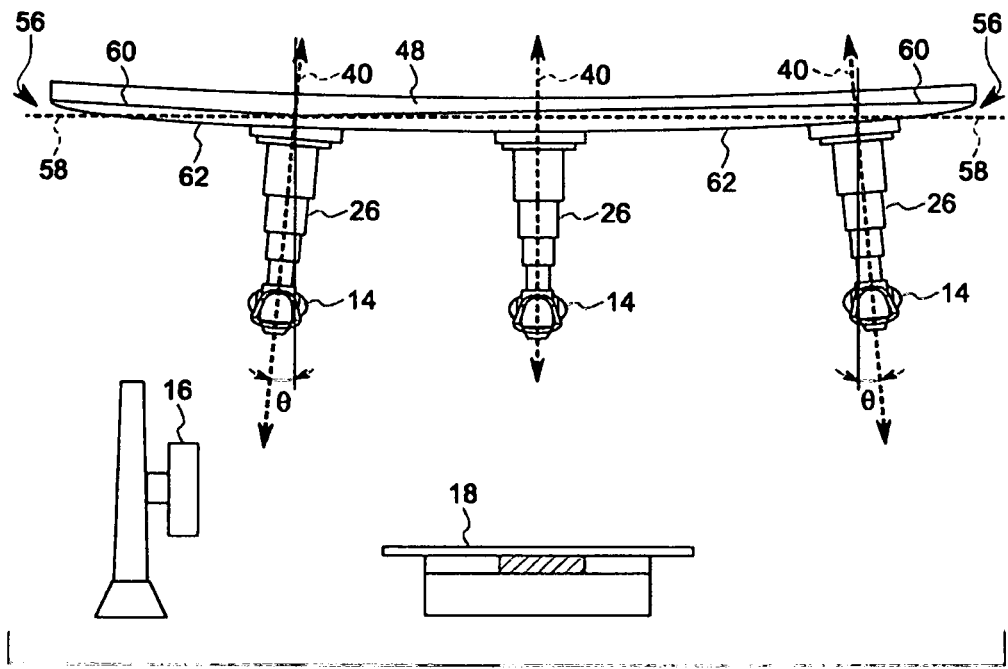
FIG. 2 is another diagram of the imaging system of FIG. 1, wherein the imaging system is subject to an angular variance, in accordance with an embodiment of the present invention.

As stated above, due to a variety of reasons, the positioning system 54 may become misaligned, e.g., due to warping and/or shifting of the ceiling 48, and/or other surface to which the OTS 22 is mounted to. For example, as depicted in FIG. 2, warping of the ceiling 48 and/or mechanical deformation of the rails 30, 32 and/or mobile arm 26, may create gaps 56 between a horizontal axis 58 of the ceiling 48, i.e., the ideal/original path which the positioning system 54 may expect/rely on, and the actual path 60 of the ceiling 48. In other words, the ceiling 48 may be curved when the positioning system 54 expects a flat surface/path, e.g., axis 58. Accordingly, as the carriage 28 traverses the horizontal 30 (FIG. 1) and/or longitudinal 32 (FIG. 1) positioning rails, symbolically represented in FIG. 2 as line 62, the X-ray source 14 traverses a curved path, as opposed to a straight path, which in turn, results in an angular misalignment of the mobile arm 26 in the z-axis 40 represented by the angle θ.

Figure 3:
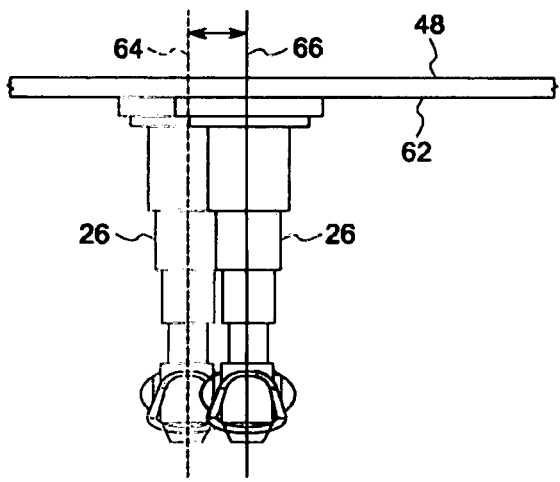
FIG. 3 is another diagram of the imaging system of FIG. 1, wherein the imaging system is subject to a translational variance, in accordance with an embodiment of the present invention.
Figure 4:
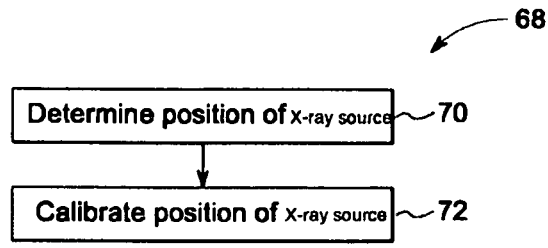
FIG. 4 is a flow chart depicting a method of calibrating the imaging system of FIG. 1 utilizing the system for calibrating the imaging system, in accordance with an embodiment of the present invention.

Similarly, as depicted in FIG. 3, shifting of the ceiling 48 may result in shifting of the horizontal 30 (FIG. 1) and/or longitudinal 32 (FIG. 1) positioning rails, again symbolically represented in FIG. 3 by line 62, which may result in a translational variance of the mobile arm 26 in the x-axis 44, y-axis 46, and/or z-axis 40. In other words, the positioning system 54 may indicate that the mobile arm 26 is at a first/intended position/coordinate 64 when the mobile arm 26 is actually at a second/actual position/coordinate 66.

Figure 6:
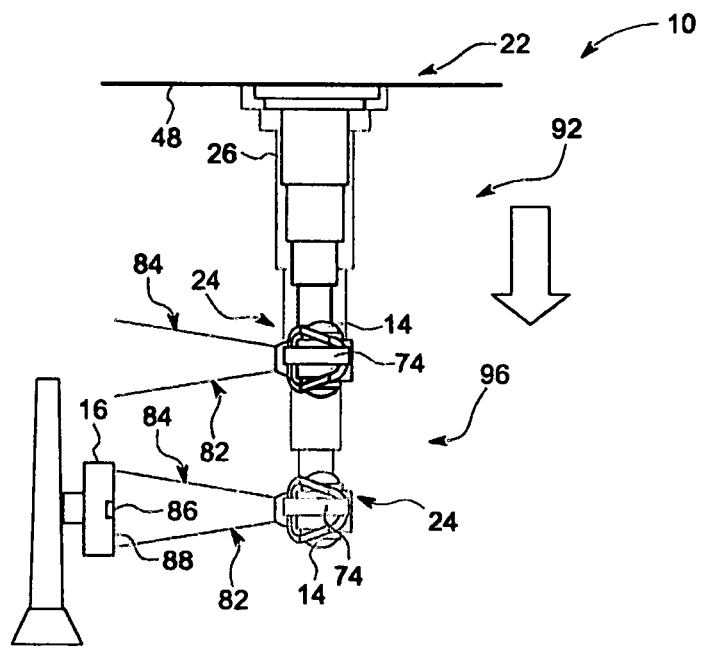
FIG. 6 is a diagram of an OTS of the imaging system of FIG. 1, wherein the OTS is moving an X-ray source of the imaging system so as to determine a position of the X-ray source with respect to a wall stand detector of the imaging system, in accordance with an embodiment of the present invention.
Figure 7:
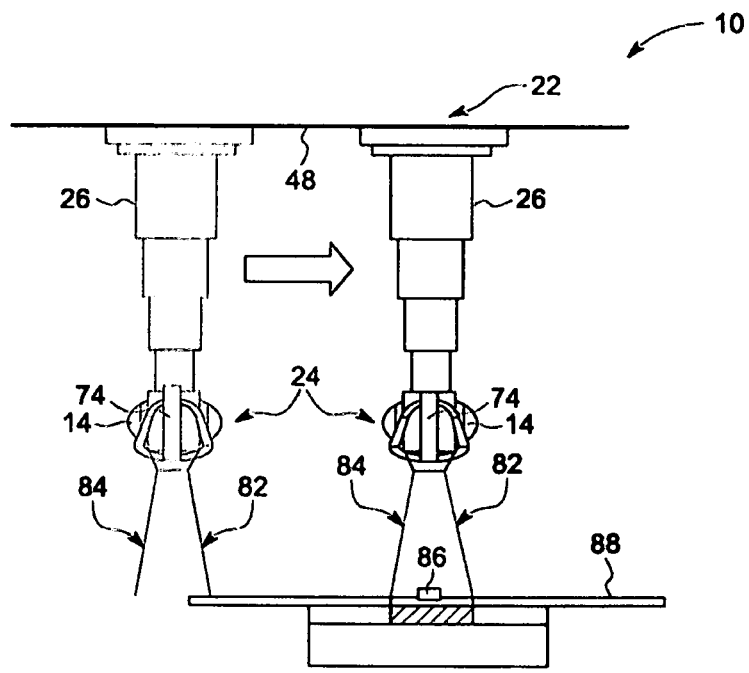
FIG. 7 is another diagram of the OTS of FIG. 6, wherein the OTS is moving the X-ray source so as to determine a position of the X-ray source with respect to a table detector of the imaging system, in accordance with an embodiment of the present invention.
Figure 8:
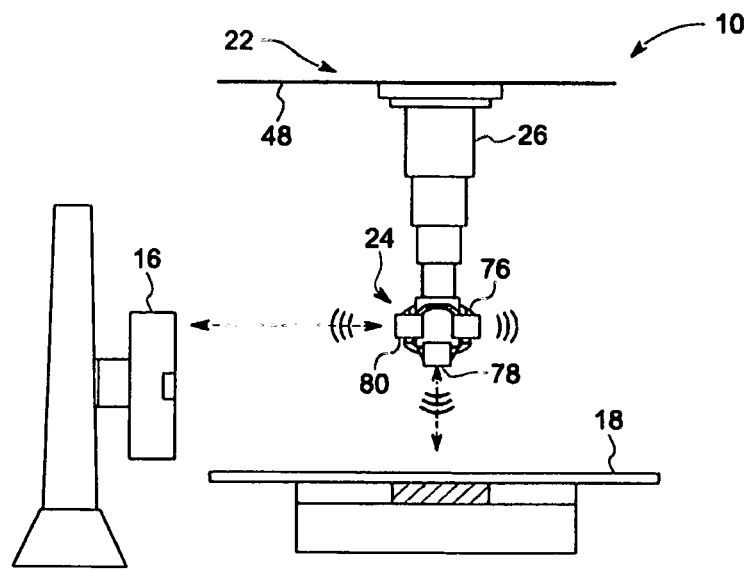
FIG. 8 is another diagram of the OTS of FIG. 6, wherein the system for calibrating the imaging system includes one or more sensors for determining a distance between the X-ray source and the wall stand detector of FIG. 6 and/or the table detector of FIG. 7, in accordance with an embodiment of the present invention.

Referring now to FIGS. 4-5 and 6-8, a method 68 (FIGS. 4 and 5) for calibrating the system 10 (FIG. 1), and/or including the positioning system 54 (FIG. 1), is shown. The method 68 includes determining 70 a position of the X-ray source 14 and calibrating 72 the position of the X-ray source 14 with respect to at least one of the detectors 16, 18 and/or the subject 12. As used herein, the term "calibrating" refers to the process of adjusting the imaging system 10, e.g., the positioning system 54 and/or FOV 84 of the X-ray source 14, to mitigate the effects of translational and/or angular variances. In embodiments, the position of the X-ray source 14 may be determined based at least in part on a sensor, e.g., a camera 74 (FIGS. 6 and 7), an ultrasound sensor 76 (FIG. 8), a laser 78 (FIG. 8), and/or an infrared sensor 80 (FIG. 8).

For example, as shown in FIG. 6, in embodiments, the system 10 may include a camera 74 disposed on the tube mounting assembly 24 and orientated such that a FOV 82 of the camera 74 substantially aligns with a FOV 84 of the X-ray source 14. The tube mounting assembly 24 may then be rotated, panned, tilted, and/or translated via the OTS 22 until the camera 74 detects a structure, e.g., one of the detectors 16 and/or 18. The controller 20 may then receive one or more images from the camera 74 and determine the location of the X-ray source 14 based at least in part on the known positions of the detected structures and/or the scale/size of the structures in the provided images. In embodiments, detection of the structures by the camera 74 may be accomplished via one or more landmarks 86, e.g., symbols, engravings, etc., disposed on the structures. Such landmarks 86 may be flush (FIG. 6) with or rise above (FIG. 7) the surface 88 of the detectors 16, 18.

Figure 5:
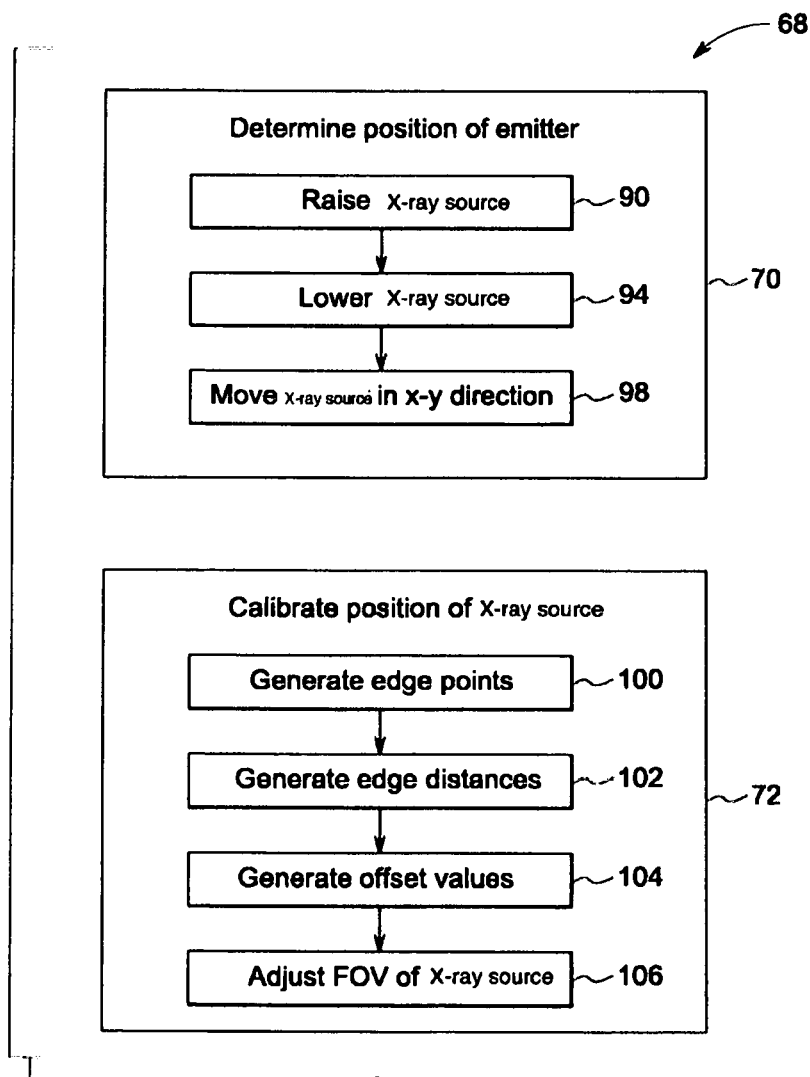
FIG. 5 is another flow chart depicting the method of FIG. 4, in accordance with an embodiment of the present invention.

Accordingly, referring to FIGS. 5 and 6, in embodiments, determining 70 the position of the X-ray source 14 may include raising/moving 90 (FIG. 5) via the OTS 22 along the z-axis 40 into a first/raised position 92 (FIG. 6), and then progressively moving/lowering 94 (FIG. 5) the X-ray source 14, via the OTS 22, along the z-axis 40 until the camera 74 reaches a second/lowered position 96 (FIG. 6) at which it detects a landmark 86 disposed on a wall stand detector 16. The X-ray source 14 may then be moved 98 (FIG. 5) along the x-axis 44 and/or y-axis 46 until the camera 74 detects a second landmark 86 (FIG. 7) on a table detector 18 (FIG. 7). As will be appreciated, by detecting the landmarks 86 on the wall stand detector 16 and/or the table detector 18, the positioning system 54 (FIG. 1) can calculate the position of the X-ray source 14. Further, as will be explained in greater detail below, in embodiments, the system 10 may calibrate 72 (FIG. 5) the position of the X-ray source 14 with respect to a detector 16 and/or 18 upon detecting the corresponding landmark 86.

For example, in embodiments, the OTS 22 may move 90, 94 and/or 98 the X-ray source 14 until the camera 74 detects the landmark 86 on the wall stand detector 16 or on the table detector 18 as being in the center of the FOV 82 of the camera 74, whereupon, the position of the X-ray source 14 is calibrated 72 with respect to the corresponding detector 16 and/or 18. As will be further understood, in embodiments, the positioning system 54 may obtain the distance of the X-ray source 14 to the detector 16 and/or 18 at the point the corresponding landmark 86 is detected via imaging processing of the feed from camera 74 and/or, as shown in FIG. 8, via a ultrasound sensor 76, laser 78, infrared sensor 80, and/or other suitable sensors.

Figure 9:
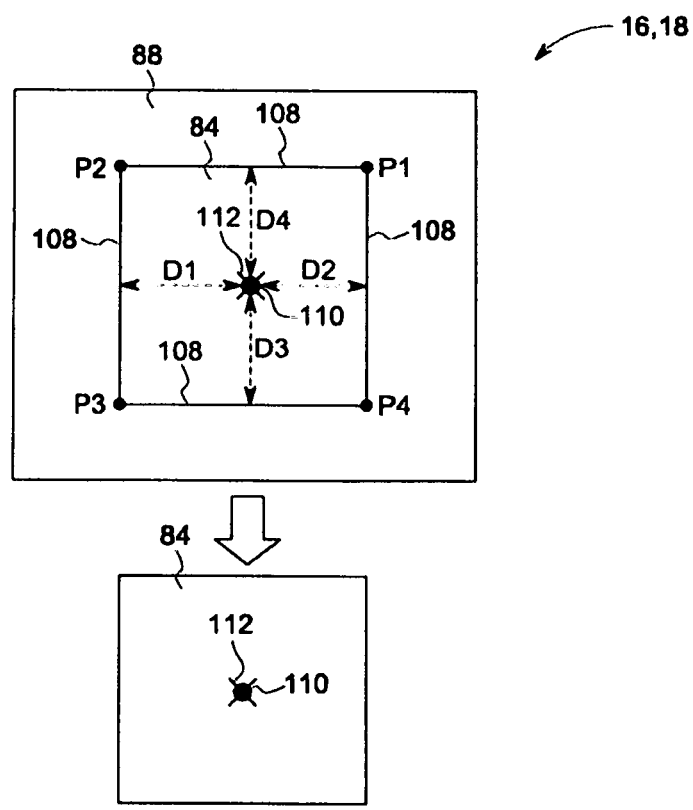
FIG. 9 is a diagram depicting a field of view ("FOV") of the X-ray source of the imaging system of FIG. 1 overlaid on a detector of the imaging system of FIG. 1, wherein a positioning system of the imaging system of FIG. 1 is calibrated, in accordance with an embodiment of the present invention.
Figure 10:
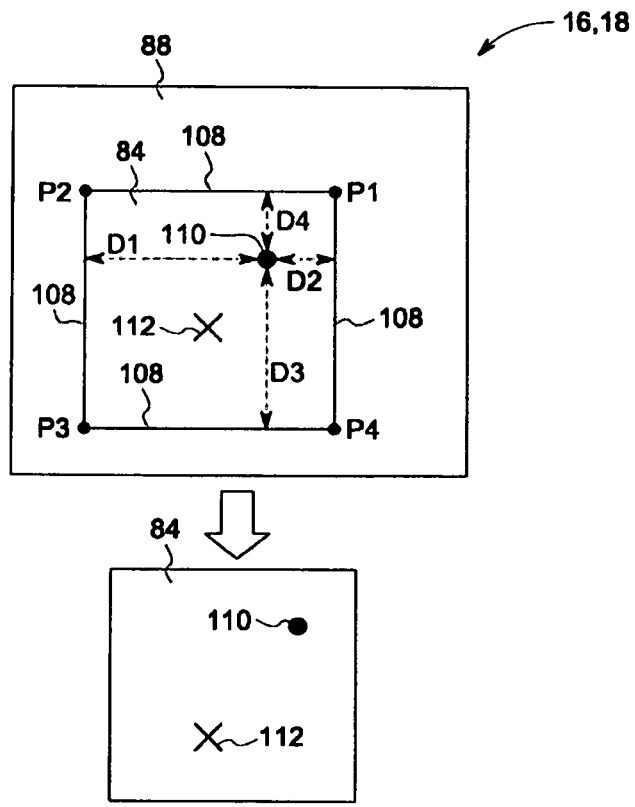
FIG. 10 is another diagram depicting the FOV of FIG. 9 overlaid on the detector, wherein the imaging system is subject to a translational variance as shown in FIG. 3, in accordance with an embodiment of the present invention.

As illustrated in FIGS. 5 and 9-10, in embodiments, calibrating 72 the position of the X-ray source 14 with respect to a detector 16, 18 may include generating 100 one or more edge points P1, P2, P3, P4; generating 102 one or more edge distances D1, D2, D3, D4; generating 104 one or more offset values via comparing the edge points P1, P2, P3, P4 to the edge distances D1, D2, D3, D4; and/or adjusting 106 the FOV 84 of the X-ray source 14 based at least in part on the offset values, e.g., adjusting parameters such as x-position, y-position, z-position, pan, tilt, of the X-ray source 14 and/or other parameters that define/effect the FOV 84. As used herein, the term "edge point" refers to a point/coordinate along the boundary 108 of the FOV 84 of the X-ray source 14; and the term "edge distance", as used herein, refers to a distance from a center 110 of a detector 16, 18 to the boundary 108 of the FOV 84 of the X-ray source 14. As will be understood, the boundary 108 of the FOV 84 of the X-ray source 14 is typically defined in part by a collimator 109 (FIG. 1) disposed in the tube mounting assembly 24 (FIG. 1), with the FOV 84 generated by taking an exposure/positioning image with the X-ray source 14 and a detector 16, 18. As used herein, the term "positioning image" refers to an image acquired via the X-ray source 14 and/or the camera 74 for the purpose of calibrating the system 10 in accordance with the methods described herein.

For example, in embodiments, the surface 88 of a detector 16, 18 may define a range of pixels/coordinates with the center 110 of the detector 16, 18 defining the origin, e.g., (0; 0) of the coordinate system for the edge distances D1, D2, D3, D4, and with a center 112 of the FOV 84 defining the origin, e.g., (0; 0) of the coordinate system for the edge points P1, P2, P3, P4. Thus, when the positioning system 54 (FIG. 1) is properly aligned/calibrated and indicates that the center 112 of the FOV 84 is aligned with the center 110 of a detector 16, 18, the values of the edge points P1, P2, P3, P4 should substantially match the values of the edge distances D1, D2, D3, D4. For example, if the resolution of the FOV 84 of the X-ray source is four-hundred by four-hundred (400×400) pixels, then the coordinates of the edge points and values of the edge distances would be as follows: P1=(200; 200); P2=(−200; 200); P3=(−200; −200); P4=(200; −200); D1=200; D2=200; D3=200; and D4=200.

Conversely, when the positioning system 54 (FIG. 1) is misaligned due to a translational variance, e.g., the ceiling 48 (FIGS. 2, 3, 6, 7, and 8) has shifted with respect to the detectors 16, 18, then the values of one or more of the edge points P1, P2, P3, P4 will not substantially match the values of the edge distances D1, D2, D3, D4. For example, as shown in FIG. 10, the positioning system 54 may indicate that the center 112 of the FOV 84 is centered on the center 110 of the detector 16, 18, when in reality, however, due to sinking and/or shifting of the ceiling 48, the center 112 of the FOV 84 may be shifted away from the center 110 of the detector 16, 18, e.g., P1=(200; 200); P2=(−200; 200); P3=(−200; −200); P4=(200; −200); while D1=214; D2=180; D3=−297; and D4=−214. In other words, the positioning system 54 believes that the FOV 84 is centered on the detector 16, 18, when in reality, the center 112 of the FOV 84 has shifted down and to the right due to shifting/sinking of the ceiling 48.

As stated above, however, embodiments of the present invention generate 104 the offset values to adjust/correct 106 for such variances. For example, in the above discussed example shown in FIG. 10, the controller 20 may generate 104 translational offset values, e.g., correction values for the positioning system 54 to adjust/shift the X-ray source 14 position along the x-axis 44, y-axis 46, and/or z-axis 40, that realign the center 112 of FOV 84 with the center 110 of the detector 16, 18. Translational offset values may be generated 104 by calculating the difference vector between the center 110 of the detector 16, 18 and the center 112 of the FOV 84.

For example, in embodiments, the offset values may be calculated based at least in part on the following equations:

$$OffsetX = Xcenter - X'center$$
$$Xcenter = (P1x - P2x)/2$$
$$X'center = (D2 - D1)/2$$
$$OffsetY = Ycenter - Y'center$$
$$Ycenter = (P1y - P4y)/2$$
$$Y'center = (D4 - D3)/2$$
$$OffsetZ = \left(\left(\frac{ABS|D2-D1|}{FOVLength}\right) - 1\right) * SID$$

Where OffsetX is the offset value for adjusting the X-ray source 14 position along the x-axis 44; OffsetY is the offset value for adjusting the X-ray source 14 position along the y-axis 46; OffsetZ is the offset value for adjusting the X-ray source 14 position along the z-axis 40; X Center is the x-coordinate of the center 112 of the FOV 84 with respect to the coordinate system defined by the center 112; and Y Center is the y-coordinate of the center 112 of the FOV 84 with respect to the coordinate system defined by the center 112.

Figure 11:
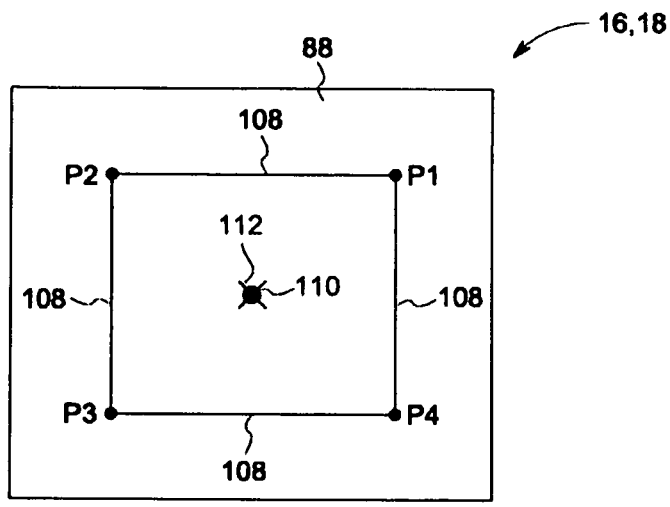
FIG. 11 is another diagram depicting the FOV of FIG. 9 overlaid on the detector, wherein the positioning system of the imaging system of FIG. 1 is calibrated, in accordance with an embodiment of the present invention.
Figure 12:
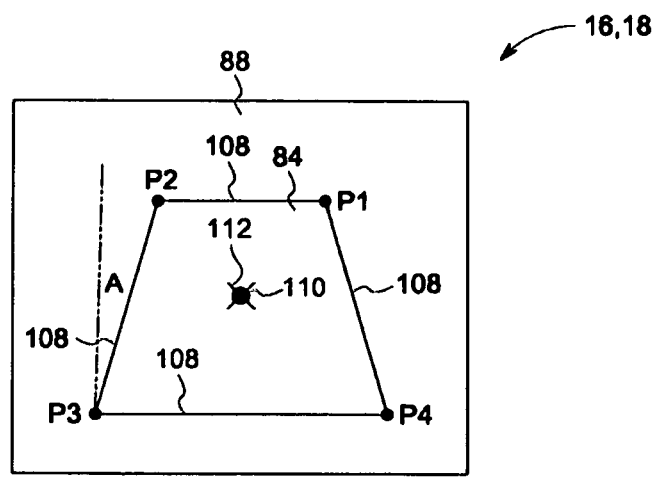
FIG. 12 is another diagram depicting the FOV of FIG. 9 overlaid on the detector, wherein the imaging system is subject to an angular variance as shown in FIG. 2, in accordance with an embodiment of the present invention.

While the above scenario concerned the correction of a translational variances, as illustrated in FIGS. 11 and 12, in embodiments, the system 10 may provide for the correction of angular variances, e.g., variances caused by a curved/warped ceiling 48 as depicted in FIG. 2. For example, as shown in FIG. 11, when the positioning system 54 is aligned and indicates that the center 112 of the FOV 84 is aligned with the center 110 of a detector 16, 18, P1, P2, P3, and P4 will form, or nearly form, a rectangle, or other shape corresponding to the expected shape of the boundary 108 of the FOV 84. Conversely, when the positioning system 54 is misaligned due to angular variances, the values P1, P2, P3, and P4 will not conform to the expected shape of the boundary 108. For example, in embodiments such as the one depicted in FIGS. 11 and 12, in which the expected shape of the boundary 108 of the X-ray source 14 is a rectangle, an angular variance may result in P1, P2, P3, and P4 forming a trapezoid (FIG. 12). In such embodiments, the offset value may be an angular offset value $_x$ which may be calculated by the following equation $$\theta \approx \arctan\left(tgA \times \frac{2D}{FOVWidth}\right)$$

where A is trapezoidal angle (FIG. 12); D is the distance between the X-ray source 14 and the surface 88 of a detector 16, 18, and FOVWidth is the width of the FOV 84.

Additionally, it will be understood that embodiments of the present invention may be used to calibrate the imaging system 10, and/or the positioning system 54, on a periodic basis, e.g., weekly, monthly, bi-annually, annually, etc. For example, the imaging system 10 may be temporarily taken out of service and transitioned/placed into a service mode, during which the imaging system 10 may be calibrated, in accordance with the methods described herein, to correct for global translational variances and/or global angular variances, e.g., long term warping and/or shrinking of the ceiling due to structural aging. In embodiments, the imaging system 10, and/or the positioning system 54, may be calibrated, in accordance with embodiments of the present invention or on a per-use basis. For example, the imaging system 10 may be calibrated while remaining in operational mode to correct for translational and/or angular variances occurring due to temporary warping and/or shifting of the ceiling due to temperature and/or humidity changes.

Figure 13:
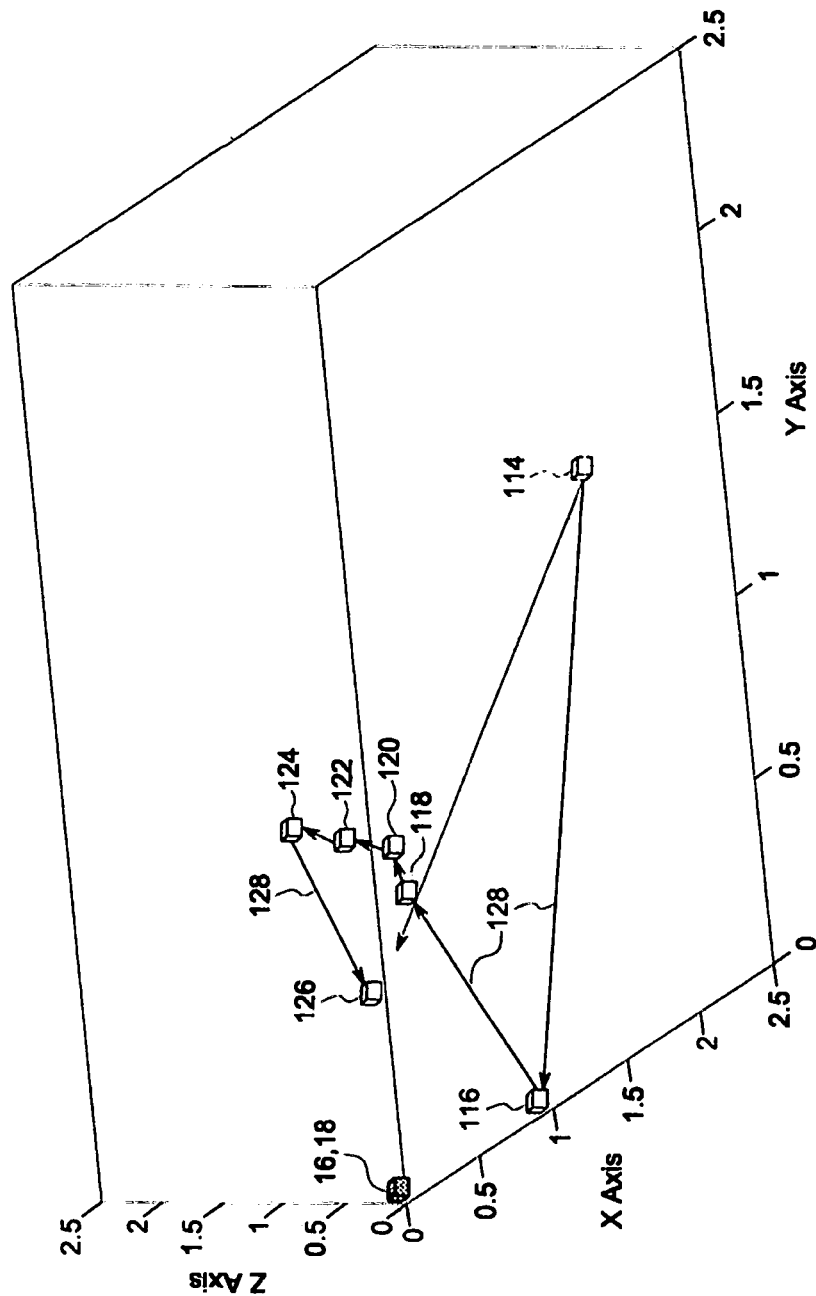
FIG. 13 is a diagram of a path for positioning the X-ray source of the imaging system of FIG. 1 at one or more calibration positions, in accordance with an embodiment of the present invention.
Figure 14:
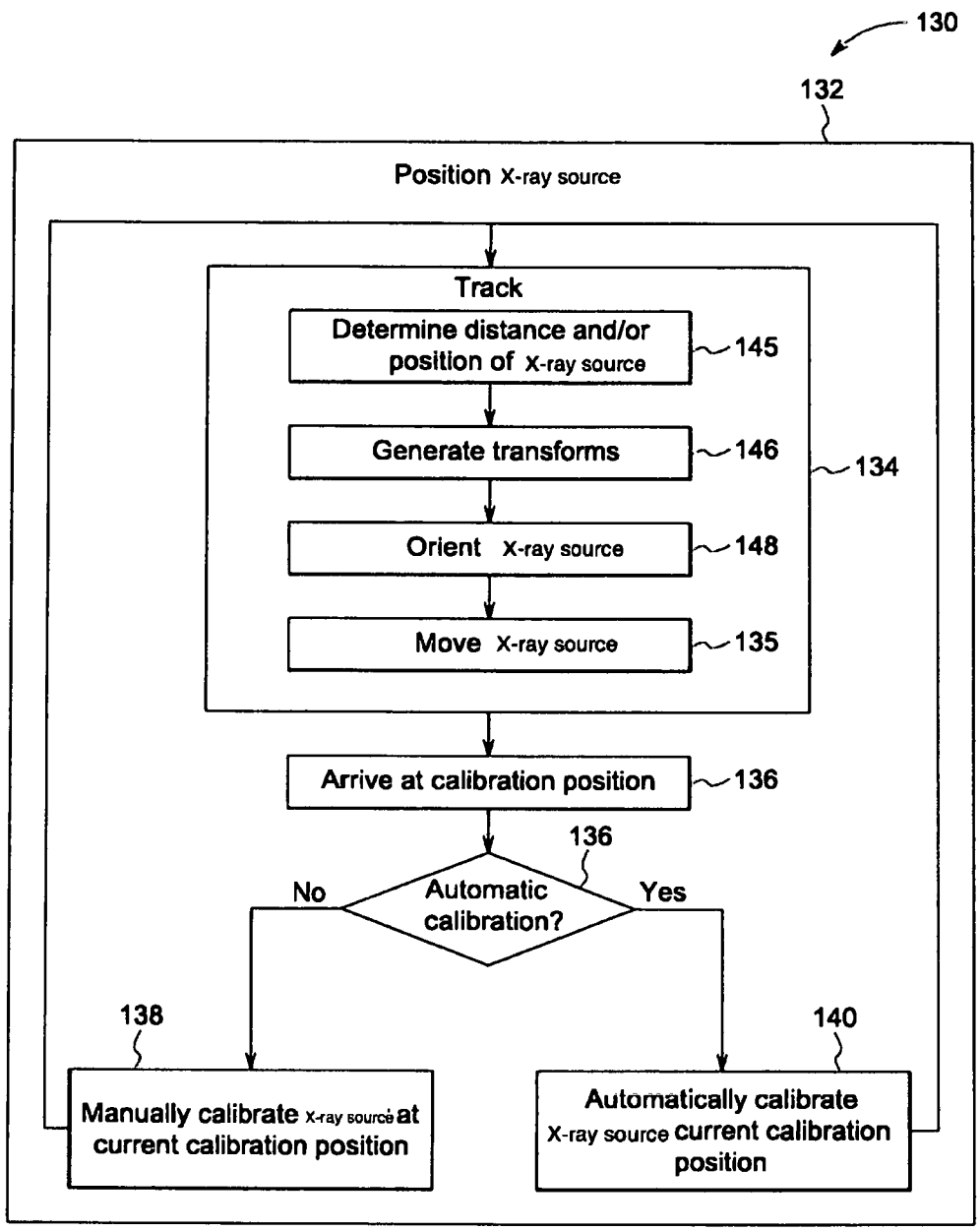
FIG. 14 is a flow chart depicting another method of calibrating the imaging system of FIG. 1 utilizing the system for calibrating the imaging system, in accordance with an embodiment of the present invention.

Referring now to FIGS. 13 and 14, embodiments of the present invention may provide for calibration of the positioning system 54 for one or more calibration positions/poses 114, 116, 118, 120, 122, 124, 126 (FIG. 13) of the X-ray source 14 along a path/trajectory 128 (FIG. 13). As will be understood, FIG. 13 depicts a representative map of the imaging system 10 and pose/calibration positions 114, 116, 118, 120, 122, 124, 126. Accordingly, a method 130 (FIG. 14) for calibrating the system 10, in accordance with an embodiment of the present invention, is shown. The method 130 includes positioning 132 the X-ray source 14 via the controller 20, and based at least in part on one or more cameras, e.g., camera 74, at/to one or more calibration positions, i.e., positions 114, 116, 118, 120, 122, 124, 126 such that the FOV 84 of the X-ray source 14 is directed substantially towards the detector 16 or 18 at each of the calibration positions 114, 116, 118, 120, 122, 124, and 126.

For example, in embodiments of the present invention, the camera 74 may send a video feed to the controller 20, which in turn, processes the received feed to detect and track 134 one of the detectors 16, 18 and/or the subject 12 as the OTS 22 moves 135 the X-ray source 14 to each of the calibration positions 114, 116, 118, 120, 122, 124, and 126.

As further shown in FIG. 13, upon arriving 136 at a calibration position, e.g., position 114, the OTS 22 may pause/stop movement of the X-ray source 14 so that a technician may manual calibrate 138 the positioning system 54. In other embodiments, the controller 20 may automatically calibrate 140 the positioning system 54 in accordance with one or more steps as discussed above with respect to method 68, e.g., generation of offset values by analyzing edge points and edge distances.

Figure 15:
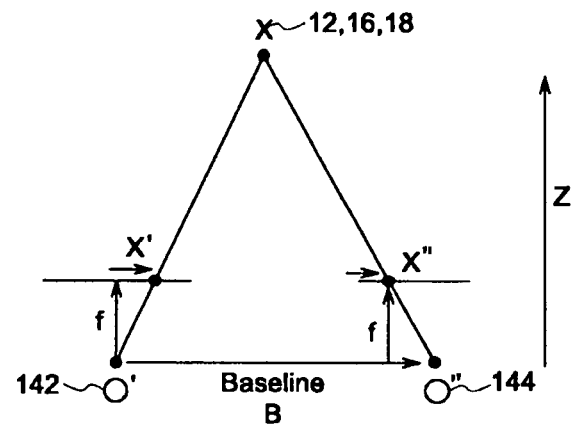
FIG. 15 is a diagram depicting a calculation of a distance of the X-ray source of the imaging system of FIG. 1 from a detector of the imaging system based at least in part on images acquired by two stereo cameras, in accordance with an embodiment of the present invention.

As shown in FIG. 15, in embodiments, the one or more cameras 74 may be two stereo cameras 142 and 144. Accordingly, the method 130 may further include determining 145 a distance Z (FIG. 15) of the X-ray source 14/cameras 142, 144, via the controller 20, to a detector 16, 18 and/or the subject 12 via the stereo cameras 142 and 144. In such embodiments, the distance Z may be derived/generated/calculated by the equation:

$$D = x' - X'' = Bf/Z$$

where x' and x" are the detected locations of the subject/detector X from stereo cameras 142 and 144, respectively; where O' and O" (FIG. 15) are the respective origins of cameras 142 and 144, f is the focal length of the stereo cameras 142, 144; and where D is disparity between the images from each camera 142 and 144.

Figure 16:
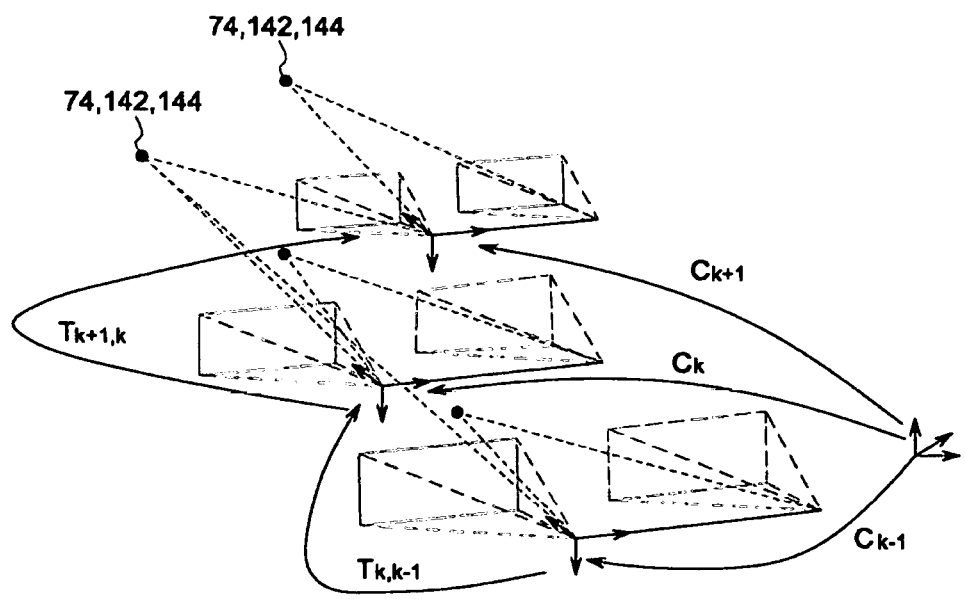
FIG. 16 is a diagram depicting a calculation of one or more trajectories for the X-ray source, wherein the trajectories move the X-ray source along the path of FIG. 13, in accordance with an embodiment of the present invention.

The method 130 may further include generating 146 motion transformations for the X-ray source 14 via the controller 20 based at least in part on frames acquired by the camera 74 or stereo cameras 142 and 144. As shown in FIG. 16, two camera positions, e.g., camera 142 and 144, at adjacent time instants k−1 and k are related by the rigid body transformation:

$$T_k = \begin{bmatrix} R_{k,k-1} & t_{k,k-1} \\ 0 & 1 \end{bmatrix}$$

As will be understood, the set $T_{0:n}=\{T_1, \ldots, T_n\}$ contains all subsequent motions, while the set of camera poses $C_{0:n}=\{C_0, \ldots, C_n\}$ contains the transformations of the camera with respect to the initial coordinate frame at k=0. Thus, motion transforms may be estimated/generated/calculated on a frame-by-frame basis as data is made available. In embodiments, generation of the motion transforms may include feature matching and tracking, which may be performed in 2D and/or 3D.

Figure 17:
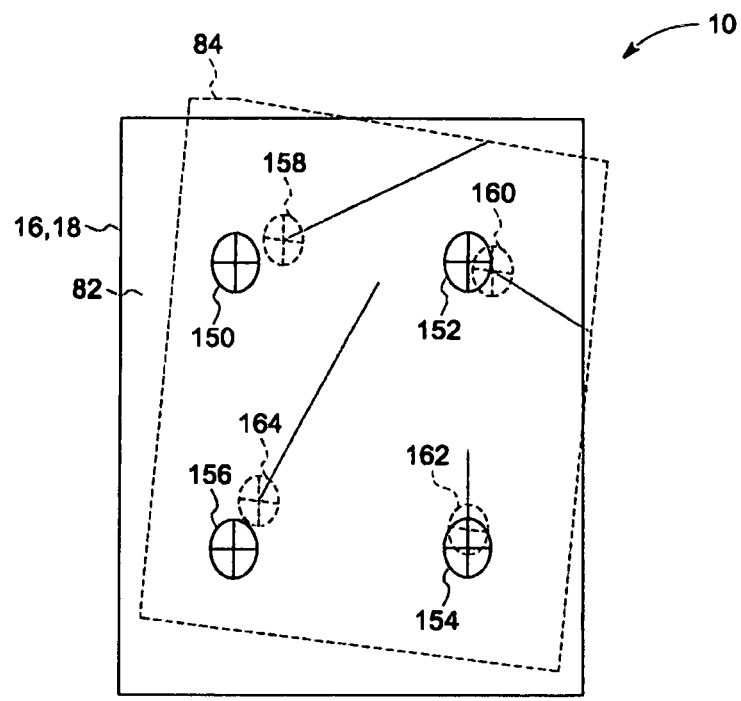
FIG. 17 is a diagram depicting a FOV of a camera of the system for calibrating the imaging system of FIG. 1 overlaid on a detector, wherein one or more virtual markers are disposed in the FOV of the camera, in accordance with an embodiment of the present invention.

As illustrated in FIG. 17, in embodiments, the method 130 may further include orientating 148 the X-ray source 14 via the controller 20 such that one or more landmarks 150, 152, 154, 156, disposed on the detector 16, 18, align with one or more corresponding virtual markers 158, 160, 162, 164 disposed within the FOV 84 of the X-ray source 14. The landmarks 150, 152, 154, 156 may be stickers, engravings, and/or other features which the cameras 74 and/or 142, 144 are capable of detecting. Tracking of the landmarks 150, 152, 154, 156 may be accomplished by analysis of frames/images received from the cameras 74 and/or 142, 144 by the controller 20, with the controller 20, in turn, calculating/generating new trajectories for the X-ray source 14, and moving the X-ray source 14 along the trajectories via the OTS 22.

Turning to FIG. 18, in embodiments, the method 130 may further include automatically thresholding 166 a detected offset of the center 112 of the FOV 84 from the center 110 of the detector. In other words, in embodiments, the method 130 may only move the X-ray source 14 and/or change the orientation of the X-ray source 14 if the difference between the center 112 of the FOV 84 and the center 110 of the detector 16, 18 exceeds a pre-determined threshold. As further shown in FIG. 18, the method 130 may also include median filtering 168 the feed from the camera 74 and/or 142, 144 for stray noise, and/or line filtering 170 detected squares within the feed from the camera 74, 142, 144. The method 130 may further include computing 180 a local centroid and offset from the detector 16, 18. In other words, in embodiments of the present invention, the controller 22 continuously attempts to align the virtual markers 158, 160, 162, 164 with the landmarks 150, 152, 154, 156 by adjusting the orientation of the X-ray source 14 as the X-ray source 14 moves along the path 128. As will be understood, with FIG. 17 depicts the virtual markers 158, 160, 162, 164 as being disposed in the FOV 84 of the X-ray source 14, it will be understood that the virtual markers 158, 160, 162, 164 may be disposed in the FOV 82 of cameras 74 and/or 144, 142.

Moving to FIG. 19, another method 174 of calibrating the imaging system 10 is shown, in accordance with an embodiment of the present invention. The method 174 includes initializing 176 the collimator and/or X-ray source 14 position to a point toward a detector 16, 18; creating 178 a dense 3D scene map; detecting 180 a target, e.g., the wall stand detector 16, from the camera 74, 142, 144 feed/image; computing 182 3D information of the detector 16, 18 position; computing 184 a desired OTS 22 position with respect to the scene map; and/or referencing 186 the scene map for one or more desired locations and the initial detector 16, 18 location. The method 174 may further include starting 188 with an initial error between a desired position and a current position of the X-ray source 14; motion controlling 190 the X-ray source 14 via the OTS 22; detecting 192 a target in a current frame of the camera 74, 142, 144 feed; and/or computing 194 3D information of the detector with the original map. The method 174 may further include updating 196 the current location in the map, and alerting a technician of an optimal path. The method 174 may further include determining 198 whether the X-ray source 14 has reached a global pose/calibration position, and if so, taking 200 an exposure and computing a collimator offset from the detector center. If the X-ray source 14 has not reached a global pose, then the method 174 may further include converting 202 a local detector offset to global 3D coordinates. After taking 200 the exposure, the method 174 may further include determining 204 if the desired local pose has been reached, and if not, converting 202 the detector offset to global 3D coordinates.

Finally, it is also to be understood that the imaging system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein, which may be accomplished in real-time. For example, as previously mentioned, the systems may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, an X-ray system is provided. The X-ray system includes an X-ray source, a detector, and a controller. The X-ray source is operative to transmit X-rays through a subject. The detector is operative to receive the X-rays. The controller is operative to determine a position of the X-ray source, and to calibrate the position of the X-ray source with respect to the detector based at least in part on a field of view of the X-ray source. In certain embodiments, the controller calibrates the position of the X-ray source with respect to the detector by: generating one or more edge points of the field of view of the X-ray source; generating one or more edge distances of the field of view with respect to a center of the detector; generating one or more offset values via comparing the one or more edge points to the one or more edge distances; and adjusting the field of view based at least in part on the one or more offset values. In certain embodiments, the one or more offset values include at least one translational offset value. In certain embodiments, the one or more offset values include an angular offset value. In certain embodiments, the controller generates the one or more edge points and the one or more edge distances based at least in part on one or more positioning images acquired via the X-ray source and the detector. In certain embodiments, the system further includes one or more sensors. In such embodiments, the controller determines the position of the X-ray source via the one or more sensors. In certain embodiments, at least one of the one or more sensors is a camera. In certain embodiments, the one or more sensors include at least one of an ultrasound sensor, a laser, and an infrared sensor.

Other embodiments provide for a method of calibrating an X-ray system. The method includes determining a position of an X-ray source of the system operative to transmit X-rays through a subject. The method further includes calibrating the position of the X-ray source with respect to a detector of the system based at least in part on a field of view of the X-ray source. The detector is operative to receive the X-rays transmitted by the X-ray source. In certain embodiments, calibrating the position of the X-ray source with respect to a detector of the system includes: generating one or more edge points of the field of view of the X-ray source; generating one or more edge distances of the field of view with respect to a center of the detector; generating one or more offset values via comparing the one or more edge points to the one or more edge distances; and adjusting the field of view based at least in part on the one or more offset values. In certain embodiments, generating one or more offset values via comparing the one or more edge points to the one or more edge distances includes generating at least one translational offset value. In certain embodiments, generating one or more offset values via comparing the one or more edge points to the one or more edge distances includes generating an angular offset value. In certain embodiments, the position of the X-ray source is determined based at least in part on one of a camera, an ultrasound sensor, a laser, and an infrared sensor.

Yet still other embodiments provide for a non-transitory computer-readable medium storing instructions. The stored instructions adapt a controller to generate one or more edge points of a field of view of an X-ray source of a system for imaging a subject with respect to a detector of the system, and to generate one or more edge distances of the field of view with respect to a center of the detector. The stored instructions further adapt the controller to generate one or more offset values via comparing the one or more edge points to the one or more edge distances, and to adjust the field of view based at least in part on the one or more offset values.

Yet still other embodiments provide for a controller for calibrating a system for imaging a subject. The controller is operative to generate one or more edge points of a field of view of an X-ray source of the system with respect to a detector of the system, and to generate one or more edge distances of the field of view with respect to a center of the detector. The controller is further operative to generate one or more offset values via comparing the one or more edge points to the one or more edge distances, and to adjust one or more parameters of the system based at least in part on the one or more offset values, the one or more parameters determining, in part, the field of view.

Yet still other embodiments provide for a system for imaging a subject. The system includes an X-ray source, a detector, at least one camera, and a controller. The X-ray source is disposed on a mobile arm and operative to transmit X-rays through the subject. The detector is operative to receive the X-rays transmitted by the X-ray source. The controller is operative to position the X-ray source via the mobile arm at one or more calibration positions based at least in part on the at least one camera such that a field of view of the X-ray source is directed substantially towards the detector at each of the calibration positions. In certain embodiments, the at least one camera includes two stereo cameras operative to determine a distance of the X-ray source to at least one of the detector and the subject. In certain embodiments, the controller is further operative to generate motion transformations for the X-ray source based at least in part on one or more frames acquired by the at least one camera. In certain embodiments, the controller is further operative to determine an initial position of the X-ray source with respect to at least one of the detector and the subject. In certain embodiments, the controller is further operative to determine a current position of the X-ray source via the camera based at least in part on one or more landmarks. In certain embodiments, the one or more landmarks are disposed on the detector. In certain embodiments, the controller is further operative to orient the X-ray source such that the one or more landmarks align with one or more corresponding virtual markers disposed in the field of view of the X-ray source.

Yet still other embodiments provide for a method of calibrating a system for imaging a subject. The method includes positioning an X-ray source of the system via a controller at one or more calibration positions based at least in part on at least one camera of the system. The X-ray source is disposed on a mobile arm and operative to transmit X-rays through the subject. A field of view of the X-ray source is directed substantially towards the detector at each of the calibration positions. In certain embodiments, the at least one camera includes two stereo cameras. In such embodiments, the method further includes determining a distance of the X-ray source via the controller to at least one of the detector and the subject via the two stereo cameras. In certain embodiments, the method further includes generating motion transformations for the X-ray source via the controller based at least in part on frames acquired by the at least one camera. In certain embodiments, the method further includes determining an initial position of the X-ray source with respect to at least one of the detector and the subject. In certain embodiments, the method further includes determining a current position of the X-ray source via the controller and the at least one camera based at least on part on one or more landmarks. In certain embodiments, the method further includes orientating the X-ray source via the controller such that the one or more landmarks align with one or more corresponding virtual markers disposed in the field of view of the X-ray source.

Yet still other embodiments provide for a non-transitory computer readable medium storing instructions. The stored instructions adapt a controller to position an X-ray source of a system for imaging a subject at one or more calibration positions based at least in part on at least one camera of the system. The X-ray source is disposed on a mobile arm and operative to transmit X-rays through the subject. A field of view of the X-ray source is directed substantially towards the detector at each of the calibration positions. In certain embodiments, the at least one camera includes two stereo cameras. In such embodiments, the stored instructions further adapt the controller to determine a distance of the X-ray source to at least one of the detector and the subject via the two stereo cameras, and to generate a motion transformation for the X-ray source based at least in part on the distance.

Accordingly, as will be appreciated, by providing for calibration of an OTS imaging system to correct for translational and/or angular variances, some embodiments of the present invention provide for improved image quality over traditional imaging systems. Further, by calibrating the OTS imaging system based on a field of view of an X-ray source and/or a camera, some embodiments of the present invention provide for an improved calibration system that is easy to integrate into existing OTS imaging systems. Further still, by correcting for translational and/or angular variances, some embodiments of the present invention provide for improved flexibility during site installation of an OTS imaging system.

Additionally, by providing for automated calibration of an OTS imaging system along one or more calibration points of a path for an OTS scanning procedure, some embodiments of the present invention provide for improved patient-throughput and/or reduced technician error over traditional imaging systems.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their subjects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. An X-ray imaging system comprising:
   an X-ray source operative to transmit X-rays through a subject;
   a detector operative to receive the X-rays;
   a controller operative to:
      determine a position of the X-ray source; and
      calibrate the position of the X-ray source with respect to the detector based at least in part on a field of view of the X-ray source;
      wherein the controller calibrates the position of the X-ray source with respect to the detector by:
         generating one or more edge points of the field of view of the X-ray source;
         generating one or more edge distances of the field of view with respect to a center of the detector;
         generating one or more offset values via comparing the one or more edge points to the one or more edge distances; and
         adjusting the field of view based at least in part on the one or more offset values.

2. The X-ray imaging system of claim 1, wherein the one or more offset values include at least one translational offset value.

3. The X-ray imaging system of claim 1, wherein the one or more offset values include an angular offset value.

4. The X-ray imaging system of claim 1, wherein the controller generates the one or more edge points and the one or more edge distances based at least in part on one or more positioning images acquired via the X-ray source and the detector.

5. The X-ray imaging system of claim 1 further comprising:
   one or more sensors;
   wherein the controller determines the position of the X-ray source via the one or more sensors.

6. The X-ray imaging system of claim 5, wherein at least one of the one or more sensors is a camera.

7. The X-ray imaging system of claim 5, wherein the one or more sensors include at least one of an ultrasound sensor, a laser, and an infrared sensor.

8. A method of calibrating an X-ray imaging system, the method comprising:
   determining a position of an X-ray source of the system operative to transmit X-rays through a subject;

calibrating the position of the X-ray source with respect to a detector of the system, based at least in part on a field of view of the X-ray source, the detector operative to receive the X-rays transmitted by the X-ray source;

wherein calibrating the position of the X-ray source with respect to a detector of the system comprises:

generating one or more edge points of the field of view of the X-ray source;

generating one or more edge distances of the field of view with respect to a center of the detector;

generating one or more offset values via comparing the one or more edge points to the one or more edge distances; and adjusting the field of view based at least in part on the one or more offset values.

9. The method of claim 8, wherein generating one or more offset values via comparing the one or more edge points to the one or more edge distances comprises:

generating at least one translational offset value.

10. The method of claim 8, wherein generating one or more offset values via comparing the one or more edge points to the one or more edge distances comprises:

generating an angular offset value.

11. The method of claim 8, wherein the position of the X-ray source is determined based at least in part on one of a camera, an ultrasound sensor, a laser, and an infrared sensor.

* * * * *